United States Patent [19]
Robinson et al.

[11] Patent Number: 5,685,848
[45] Date of Patent: *Nov. 11, 1997

[54] BALLOON CATHETER INFLATION DEVICE

[75] Inventors: David B. Robinson, Chanhassen; Daniel O. Adams, Blaine; William H. Penny, St. Anthony; Gerald G. Voegele, St. Bonifacius, all of Minn.

[73] Assignee: SCIMED Life Systems, Inc., Maple Grove, Minn.

[*] Notice: The term of this patent shall not extend beyond the expiration date of Pat. No. 5,019,041.

[21] Appl. No.: 475,760

[22] Filed: Jun. 7, 1995

Related U.S. Application Data

[63] Continuation of Ser. No. 227,026, Apr. 13, 1994, abandoned, which is a continuation of Ser. No. 861,955, Apr. 1, 1992, Pat. No. 5,429,606, which is a continuation of Ser. No. 482,828, Feb. 21, 1990, Pat. No. 5,147,300, which is a division of Ser. No. 165,600, Mar. 8, 1988, Pat. No. 5,019,041.

[51] Int. Cl.⁶ ........................................................ A61M 29/00
[52] U.S. Cl. ........................................................ 604/97; 368/10
[58] Field of Search ........................ 604/97–100, 187, 604/192, 162, 96, 101–103; 606/192–194; 368/10, 316, 71

[56] References Cited

U.S. PATENT DOCUMENTS

| | | |
|---|---|---|
| D. 274,470 | 6/1984 | Lundquist . |
| 3,138,161 | 6/1964 | Allen . |
| 3,698,381 | 10/1972 | Federico et al. . |
| 3,794,026 | 2/1974 | Jacobs . |
| 3,895,633 | 7/1975 | Bartner et al. . |
| 3,937,219 | 2/1976 | Karakashian . |
| 3,995,263 | 11/1976 | Shreve et al. . |
| 4,016,871 | 4/1977 | Schiff . |
| 4,078,562 | 3/1978 | Friedman . |
| 4,107,995 | 8/1978 | Ligman et al. . |
| 4,122,836 | 10/1978 | Burnett . |
| 4,231,715 | 11/1980 | Gleichner . |
| 4,244,366 | 1/1981 | Raines . |
| 4,250,572 | 2/1981 | Yoshida . |
| 4,275,729 | 6/1981 | Silver et al. ............ 604/211 |
| 4,332,254 | 6/1982 | Lundquist . |
| 4,370,982 | 2/1983 | Reilly . |
| 4,407,271 | 10/1983 | Schiff . |
| 4,418,392 | 11/1983 | Hata . |
| 4,429,724 | 2/1984 | Dorros et al. . |
| 4,439,185 | 3/1984 | Lundquist . |
| 4,443,216 | 4/1984 | Chappell . |
| 4,446,715 | 5/1984 | Bailey et al. . |
| 4,464,171 | 8/1984 | Garwin . |
| 4,502,490 | 3/1985 | Evans et al. . |

(List continued on next page.)

OTHER PUBLICATIONS

"Balloon Catheters and Transluminal Dilatation: Technical Considerations", John Abele, *American Journal of Roentgenology*, vol. 135, pp. 901–906, Nov. 1980.

Package Description of Indeflator™, mfg. by Advanced Cardiovascular Systems, Inc., 1982.

2-pg. brochure re. USCI Disposable Inflation Device from C.R.Bard, Inc.

2-pg. brochure re. USCI Wizard™ Disposable Inflation Device from C.R.Bard, Inc.

Merit Medical® publication, Intelliflator™, Inflation System, 1989.

Intelliflator™, Inflation System Monitor, Instruction Manual, Darla R. Gill and Steven R. Taylor, Merit Medical Systems, Inc., Nov. 22, 1989.

*Primary Examiner*—Mark Bockelman
*Attorney, Agent, or Firm*—Robert E. Atkinson

[57] ABSTRACT

A pressure device for use with a balloon angioplasty catheter includes a housing, a syringe body, rubber stopper and a pressure gauge. The rubber stopper is connected to a threaded plunger leading to a handle. The threaded plunger is engaged by a half nut. The half nut may also be disengaged. A forward located thumb button controls the engagement of the half nut with the threaded plunger. The initial operation of the thumb button also irreversibly illuminates the pressure gauge.

3 Claims, 7 Drawing Sheets

U.S. PATENT DOCUMENTS

| | | |
|---|---|---|
| 4,522,194 | 6/1985 | Normann . |
| 4,522,195 | 6/1985 | Schiff . |
| 4,557,269 | 12/1985 | Reynolds et al. . |
| 4,561,856 | 12/1985 | Cochran . |
| 4,583,974 | 4/1986 | Kokernak . |
| 4,585,010 | 4/1986 | Ascer et al. . |
| 4,600,015 | 7/1986 | Evans et al. . |
| 4,610,256 | 9/1986 | Wallace . |
| 4,631,960 | 12/1986 | Wögerbauer . |
| 4,634,431 | 1/1987 | Whitney et al. . |
| 4,651,738 | 3/1987 | Demer et al. . |
| 4,655,749 | 4/1987 | Fischione . |
| 4,672,974 | 6/1987 | Lee . |
| 4,710,179 | 12/1987 | Haber et al. . |
| 4,723,938 | 2/1988 | Goodin et al. . |
| 4,733,669 | 3/1988 | Segal . |
| 4,740,203 | 4/1988 | Hoskins et al. . |
| 4,743,230 | 5/1988 | Nordquest . |
| 4,758,223 | 7/1988 | Rydell . |
| 4,781,192 | 11/1988 | Demer . |
| 4,787,891 | 11/1988 | Levin et al. . |
| 4,795,431 | 1/1989 | Walling . |
| 4,796,606 | 1/1989 | Mushika . |
| 4,802,550 | 2/1989 | Poore . |
| 4,808,165 | 2/1989 | Carr . |
| 4,808,167 | 2/1989 | Mann et al. . |
| 4,825,876 | 5/1989 | Beard . |
| 4,832,692 | 5/1989 | Box et al. . |
| 4,838,864 | 6/1989 | Peterson . |
| 4,872,483 | 10/1989 | Shah . |
| 4,906,244 | 3/1990 | Pinchuk et al. . |
| 4,919,121 | 4/1990 | Rydell et al. . |
| 4,929,238 | 5/1990 | Baum . |
| 4,976,725 | 12/1990 | Chin et al. . |
| 5,015,233 | 5/1991 | McGough et al. . |
| 5,019,041 | 5/1991 | Robinson et al. . |
| 5,021,046 | 6/1991 | Wallace . |
| 5,024,668 | 6/1991 | Peters et al. . |
| 5,057,078 | 10/1991 | Foote et al. . |
| 5,084,060 | 1/1992 | Freund et al. . |
| 5,135,488 | 8/1992 | Foote et al. . |
| 5,147,300 | 9/1992 | Robinson et al. . |
| 5,152,776 | 10/1992 | Pinchuk . |
| 5,201,753 | 4/1993 | Lampropoulos et al. . |
| 5,209,732 | 5/1993 | Lampropoulos et al. . |
| 5,259,838 | 11/1993 | Taylor et al. . |

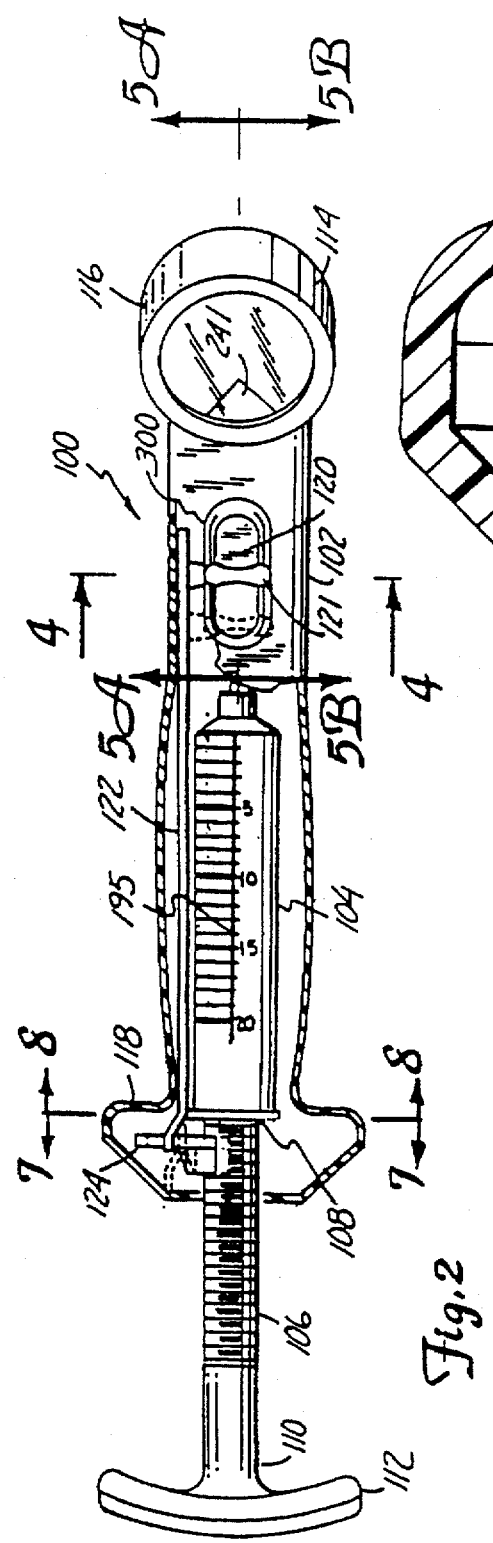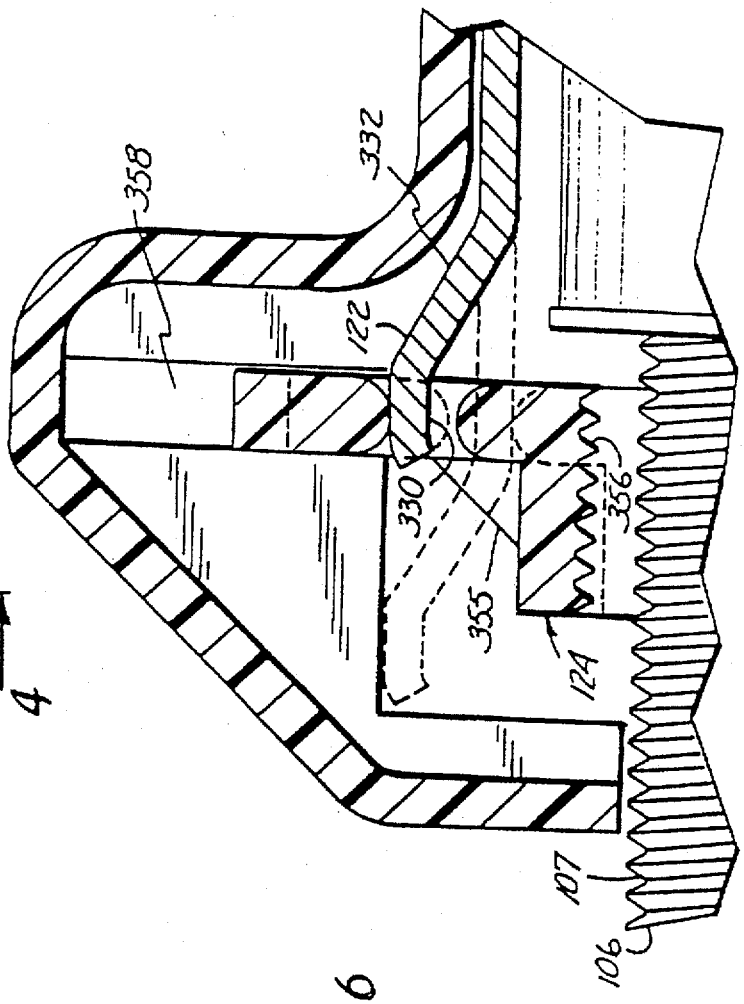

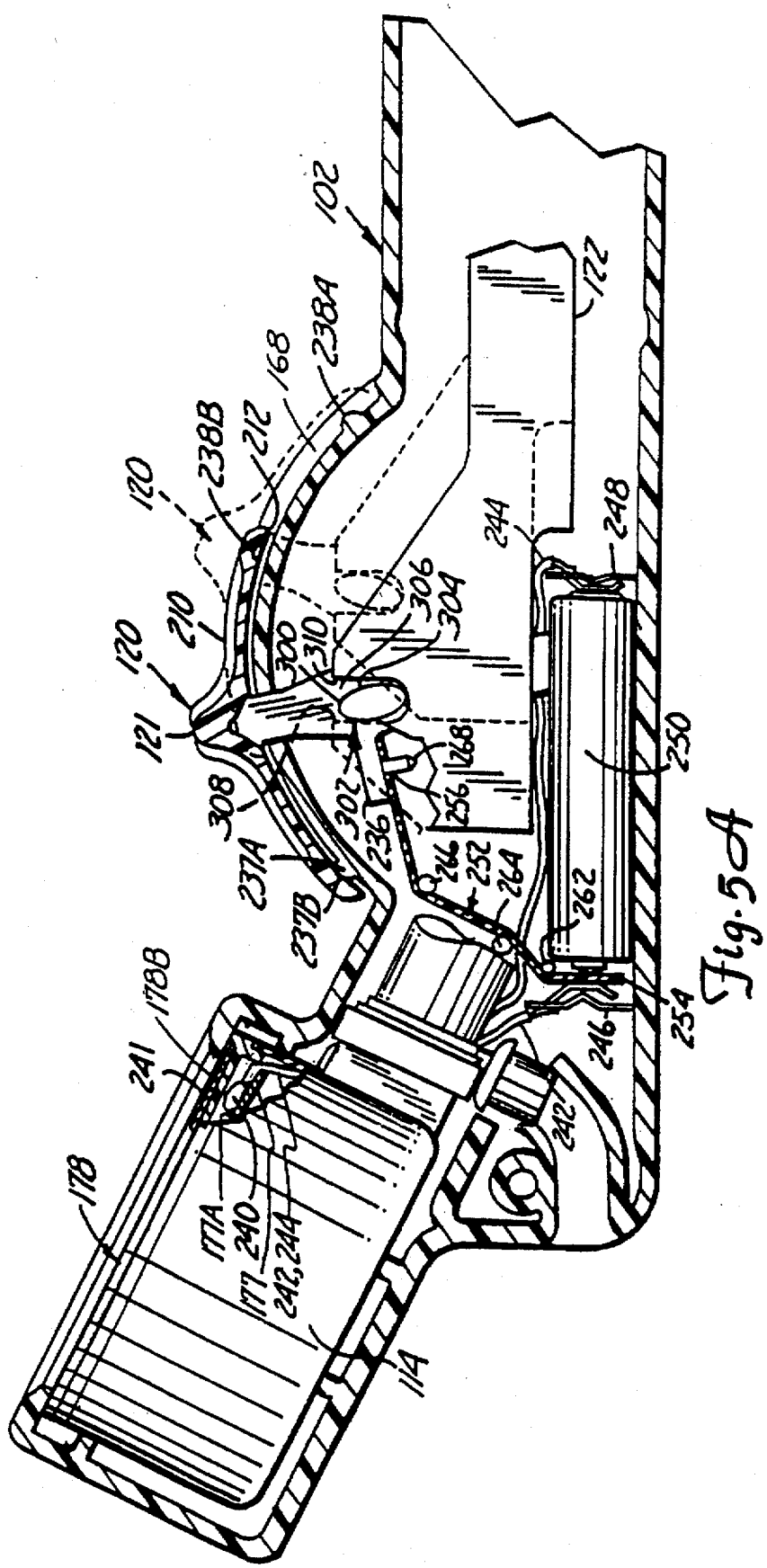

BALLOON CATHETER INFLATION DEVICE

This is a continuation of application Ser. No. 08/227,026, filed on Apr. 13, 1994, abandoned which is a continuation of application Ser. No. 07/861,955, filed on Apr. 1, 1992, now U.S. Pat. No. 5,429,606 which is a continuation of application Ser. No. 07/482,828, filed on Feb. 21, 1990, now U.S. Pat. No. 5,147,300, issued on Sep. 15, 1992, which is a divisional of application Ser. No. 07/165,600, filed on Mar. 8, 1988, now U.S. Pat. No. 5,019,041, issued on May 28, 1991.

BACKGROUND OF THE INVENTION

1. Field of the Invention

The present invention provides an apparatus and method for injecting fluid into a balloon catheter and a device for controlling the rate and pressure of fluid injection. Such catheters, when inflated by the injected fluid, are conventionally used for the purpose of percutaneous transluminal angioplasty.

2. Description of the Prior Art

Angioplasty is a procedure for dilating arteries which are occluded or blocked. The dialation procedure is especially useful for cases of coronary artery obstructions. A special catheter is used which carries a balloon at the distal end. To re-shape an occluded artery, the balloon is inflated, for instance, by being filled and pressurized with a radiopaque fluid.

An early practitioner of the angioplasty procedure was Dr. Andreas Gruntzig of the University of Zurich. The procedure developed by Dr. Gruntzig uses a special double lumen catheter. The first lumen allows passage of a guide wire. The second lumen connects to the balloon at the distal end of the catheter, which is generally filled and pressurized with diluted contrast media. Briefly, the procedure involves inserting a guide wire into a blood vessel to be dilated and advancing the guide wire to and past the block. Next, a balloon catheter is inserted along the guide wire and advanced to the most distal portion of the block or occlusion. Then, the balloon is inflated to reform the blockage material against the artery wall. The dilated balloon creates a smooth increased-diameter inner lumen in the artery. After dilation, the balloon is collapsed and retracted. The site of the former obstruction is examined, and, if necessary, the procedure is repeated until the entire segment of the artery is dilated.

The purpose of an angioplasty inflation device is to make the balloon inflation task easier and safer. One conventional procedure is to use a syringe to expand the balloon with radiopaque dye, while watching the balloon on an x-ray monitor. An operator proceeds by judging the relative balloon size, without knowing the balloon pressure; however, the balloon may rupture if its bursting pressure is exceeded.

A well-known approach to measuring the pressure of fluid inflating the balloon is to interpose a T-fitting between the delivery end of the syringe and the balloon. In this approach, a tire pressure-type gauge or other pressure indicator is connected to the-T-fitting and measures the pressure exerted by the fluid.

Typically, the angioplasty procedure is performed under relatively low level illumination to facilitate viewing the radiopaque contract fluid on the x-ray monitor. Unfortunately, this results in difficulty in reading the pressure indicators. Additionally, since the inflated balloon entirely blocks the artery to the passage of blood, time is a critical factor in the procedure. Further, the operating physician generates and controls the inflation force on the syringe, so physician fatigue is a negative factor in the procedure.

A representative example of the prior art is provided by U.S. Pat. No. 4,439,185 to Lundquist which discloses an inflation and deflation device adapted to be used by a human hand.

The device of Lundquist includes a stop cock and an optional regulator. The preferred syringe of Lundquist has a capacity of approximately 10 cc. Lundquist teaches the use of the stop cock to maintain a predetermined pressure, thereby freeing the surgeons hands from applying pressure. A single hand may create the force that moves the piston in the syringe body, however, a second hand must be used to turn the stop cock. In an alternative embodiment, Lundquist discloses a nut threaded into a fitting and a knob mounted on a head. Pressure may be applied by turning the head. A dial-type pressure gauge is threaded onto a nipple connected to the regulator.

All of the Lundquist embodiments include a "T" shaped handle large enough so that all the fingers of the hand can grasp the handle. In addition, the portion which is adapted to be engaged by the palm is rounded to fit the palm of the hand.

U.S. Pat. No. 4,332,254 to Lundquist teaches a system for filling and inflating and deflating a balloon-type dilating catheter used in performing coronary angioplasty procedures. The device includes a primary and secondary fluid pulp assembly. Lundquist also discloses replacing a mechanical dial pressure gauge with a remote electronic pressure readout arrangement.

U.S. Pat. No. 4,244,366 to Raines discloses a syringe stroke controlling mechanism including a gripping member encircling a syringe barrel and a cap on the plunger of the syringe. In an alternative embodiment, a fastener or nut is disclosed to permit rapid stroke adjustment while retaining fine adjustment features. The nut is moved out of engagement to execute the gross adjustment, and snapped back on a threaded rod so that the threads engage the threads of the metering rod. Fine adjustments of the plunger position are made by turning the nut with the threads engaged.

U.S. Pat. No. 4,655,749 to Fischione discloses an angioplasty pressure controller including a drive screw which is connected to a piston in a cylinder and arranged for fine adjustment by turning the drive screw. An engagement slide provides a rapid means to create pressure or vacuum.

U.S. Pat. No. 4,370,982 to Reilly discloses an apparatus for injecting and controlling the pressure of fluid being injected into a catheter. The apparatus provides a pressure measuring system that includes a housing for releasably and slidably holding the barrel of the syringe used to deliver fluid into the balloon catheter; and a device for measuring and indicating fluid pressure in the syringe barrel, which is also the balloon pressure. The Reilly pressure measuring system indirectly measures pressure changes of fluid in the syringe barrel by sensing movement of the barrel as a result of fluid pressure changes.

Reilly also discloses a trigger engagement of the threaded sliding barrel. An engager button has a plurality of shaped members designed to fit the grooves or between lands on the threaded portion of a bolt. The button includes a recessed portion that is engaged by a pin to interconnect the button and the housing. The button is pivotable about a pin to move the raised portion into and out of engagement with the grooves on the bolt.

U.S. Pat. No. 4,429,724 to Dorros et al. discloses a pressure generator for intravascular dilators including a ram and a syringe holder. A screw drive having a large mechanical advantage is coupled for advancing the ram at a controlled rate. A coupler at one end of the ram is adapted to engage one end of the syringe plunger. The pressure generator may be provided with a pistol grip and the ram may be calibrated for direct pressure readout.

SUMMARY OF THE INVENTION

The invention is a pressure device for use with a balloon angioplasty catheter. The device includes a housing, a syringe body, a rubber stopper and a pressure gauge. The rubber stopper is connected to a threaded plunger leading to a handle. The threaded plunger is alternatively engaged by a half nut. The half nut is controlled by a forward located thumb button. The thumb button also serves as a single use switch to illuminate the pressure gauge.

BRIEF DESCRIPTION OF THE DRAWINGS

FIG. 2 is a top view of the preferred embodiment with the handle extended and portions of the housing removed.

FIGS. 5A and 5B are partial sectional views along line 5—5 of FIG. 2.

FIG. 6 is an enlarged sectional view of a portion of FIG. 2.

DETAILED DESCRIPTION OF THE PREFERRED EMBODIMENTS

Figure 1:
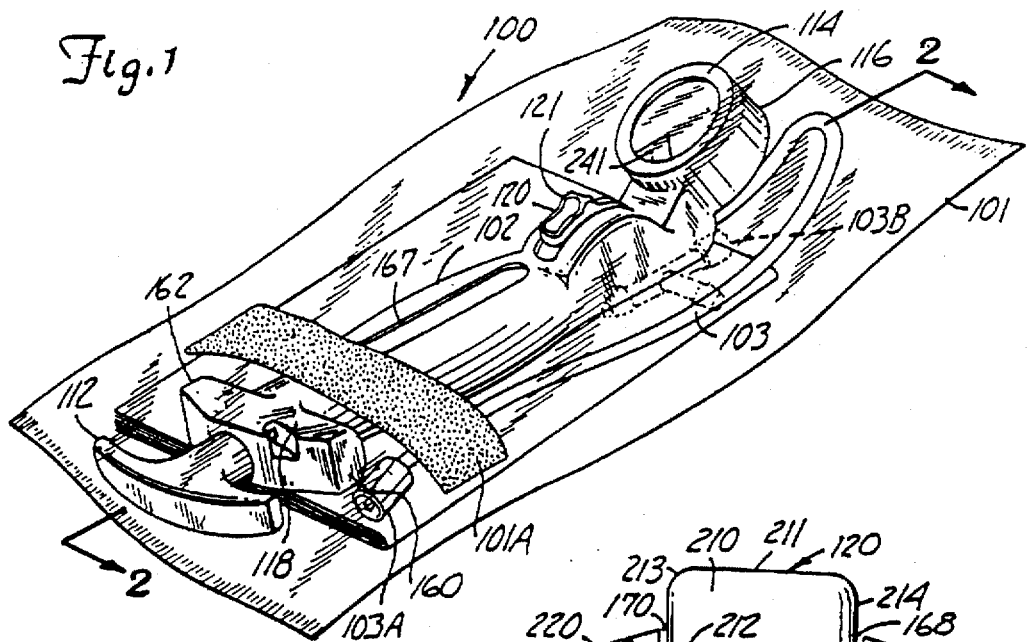
FIG. 1 is a perspective view of the preferred embodiment packaged as a kit.

In FIG. 1, the balloon catheter inflation device of this invention is generally shown at 100. The device 100 includes a housing 102 with a distal end 116 and a proximal end 118. A catheter connecting tube 103 is attached near the distal end 116. A swivel luer-lock connector 103A is located on the opposite end of the catheter connecting tube 103 and serves to connect a catheter (not shown). A three-way valve 103B, shown in dotted outline at 103B, may be optionally incorporated at the connector 103A to aid in eliminating air while priming the catheter. The device 100 also includes a handle 112 extending proximally from the housing 102, a pressure gauge 114 located distally on the housing 102 and a thumb button 120 adjacent the pressure gauge 114. The thumb button 120 includes a transverse shoulder 121 to facilitate movement by a physician's thumb. The housing 102 also includes a viewing window 167 located proximally from the thumb button 120. The device 100 may be packaged as a kit in an envelope 101 including a porous window 101A, preferably formed of Tyvek (i.e., available from DuPont; Willmington, Del.). In a most preferred embodiment, the envelope 101 is a "blister pack" arrangement.

A syringe body 104, as illustrated in FIG. 2, is fitted within the housing 102. A threaded plunger 106 has a distal end 108 (FIG. 3) inserted in the syringe body 104 and a proximal end 110 connected to the handle 112. The pressure gauge 114 is located on the distal end 116 of the housing 102. The thumb button 120 is also located upon the housing 102 adjacent to the distal end 116. The thumb button 120 is positioned along an actuator blade 122 which in turn extends to a half nut 124 located in the proximal end 118 of the housing 102.

Figure 3:
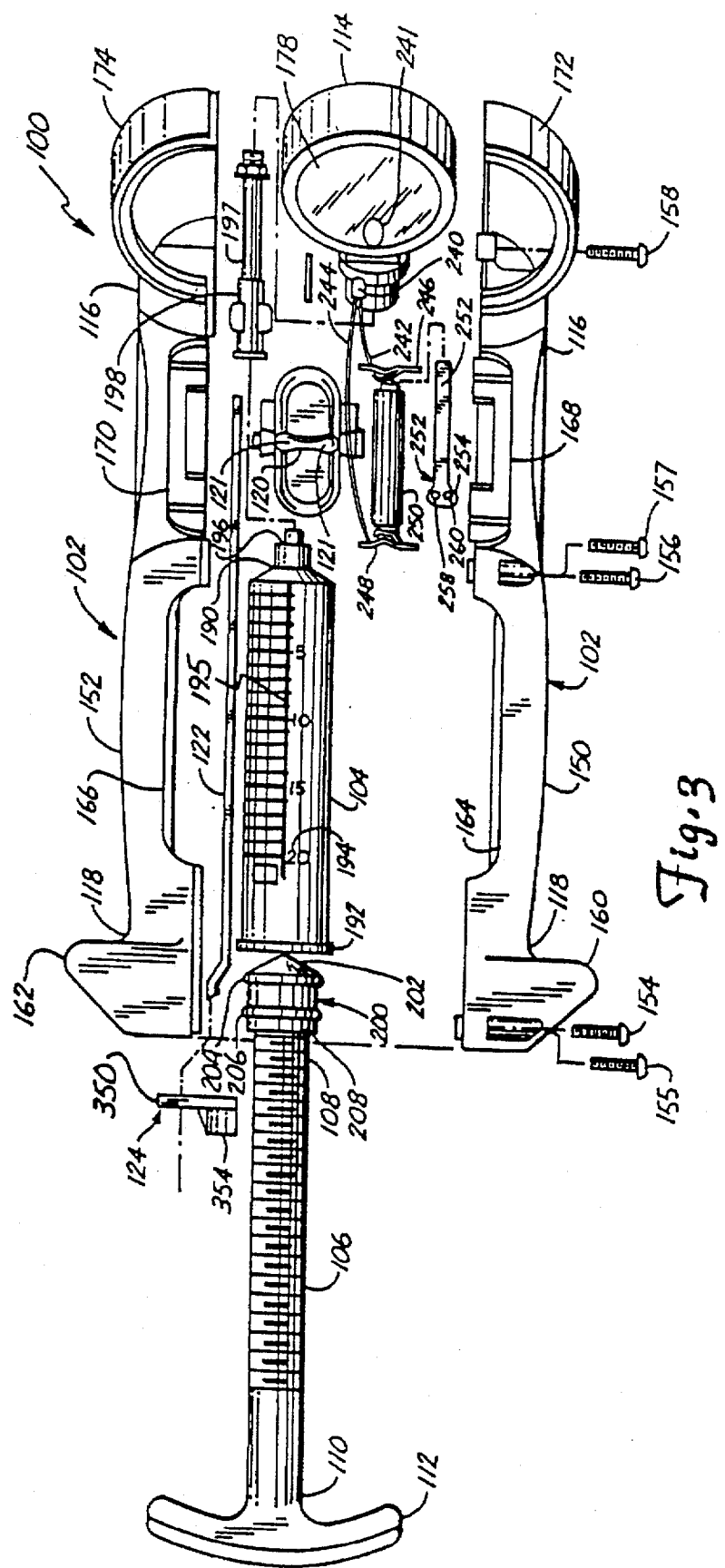
FIG. 3 is an exploded top view of the preferred embodiment.

The housing 102, as illustrated in FIG. 3, is formed of a right half 150 and a left half 152. The right half 150 of the housing 102 is secured to the left half 152 of the housing 102 by two proximal screws 154 and 155, by two central screws 156 and 157, and by a single distal screw 158. Preferably the screws are #4×½ plastic thread cutting screws. During assembly, the screws 154–158 are inserted through lateral holes in the right half 150 and cut threads within similarly located, slightly undersized holes (not shown) in the left half 152. As the screws 154–158 are tightened; the right 150 and left half 152 are drawn together to form the housing 102.

On the proximal end 118 of the right half 150 is an extension 160 which projects laterally outward from the right half 150. A similar extension 162 projects laterally outward from the proximal end 118 of the left half 152. When assembled, the two extensions 160 and 162 prevent the housing 102 from being driven distally from the gripping hand of a physician. Preferably the housing 102 is formed of molded polycarbonate and the handle 112 is formed of molded acetal. Additionally, the exterior surfaces of the housing 102 are textured to facilitate gripping of the device. A similar textured surface is included on the handle 112.

A leftward facing notch 164 on the right half 150 of the housing 102 and a complementary rightward facing notch 166 on the left half 152 of the housing 102 define the viewing window 167 of FIG. 1. The viewing window 167 allows observation of the syringe body 104 of FIG. 2 fitted within the housing 102. The viewing window 167 faces upward such that the syringe body 104 and the gauge 114 may be simultaneously observed by a physician. An inset or recess 168 of FIG. 3 is located on the right half 150 of the housing 102. A complementary inset or recess 170 is located on the left half 152 of the housing 102. Together the insets 168 and 170 define a track in which the thumb button 120 is guided.

A gauge housing portion 172 is located on the distal end 116 of the right half 150 of the housing 102. A complementary gauge housing portion 174 is located on the distal end 116 of the left half 152 of the housing 102. When assembled, the two halves of the gauge housing 172 and 174 form a cylindrical housing for the gauge 114. The cylindrical housing formed by the two halves 172 and 174 is inclined with respect to the housing 102 such that the bezel or lens 178 forms an angle of approximately 25° with respect to the syringe body 104.

The syringe body 104 is fitted within the housing 102. The syringe body 104 is generally cylindrically shaped and has a distal end 190 and a proximal end 192. Longitudinally arranged on the syringe body are a series of indicia 194, having a central line 195. These indicia 194 are visible through the viewing window 167 formed by notches 164 and 166 of the housing 102. The syringe body 104 is generally transparent, or alternatively, translucent such that liquid contents are visible through the syringe body 104. During use of the device 100, the combination of the viewing window 167, the indicia 194 and the transparent or translucent quality of the syringe body 104 allows a physician to readily estimate the volume of liquid contents. The syringe body 104 also includes a male luer-lock fitting 196 at its distal end 190. A tube 197 with a female luer-lock fitting 198 is connected to the syringe body 104 by the luer-lock fitting 196 and 198 and provides a fluid connection between the syringe body 104 and the gauge 114.

Figure 8:
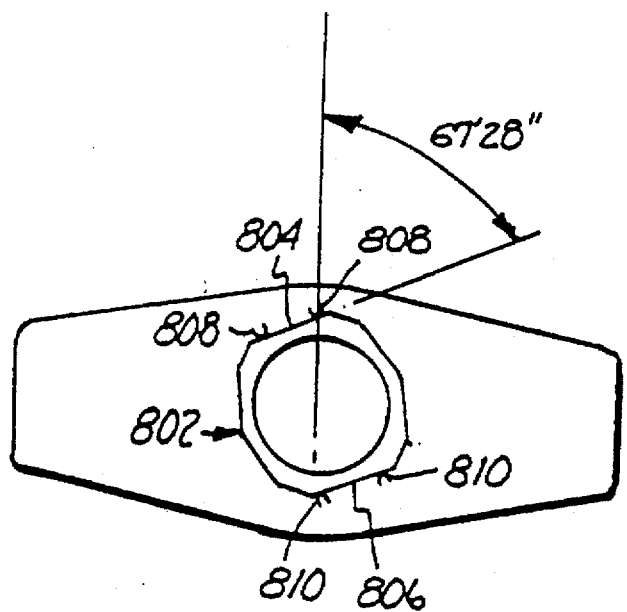
FIG. 8 is a sectional view at line 8—8 of FIG. 2.

Preferably, the proximal end 192 of the syringe body 104, as shown in FIG. 8, includes a flange 802. The flange 802 has a pair of parallel flats 804 and 806 which interact with two pair of projections 808 and 810, respectively, in the housing 102 to maintain the relationship between the indicia 194 on the syringe body 104 and the viewing window 167 of the housing 102. The syringe body 104 is preferably formed from a disposable, plastic 20 cc syringe by cutting down an original, larger rear flange. A suitable 20 cc syringe is #301031 Becton-Dickinson or equivalent, on which the flats 804 and 806 are cut at an angle of approximately 67.28° relative to the central line 195 of the indicia 194.

The syringe rubber stopper 200, as shown in FIG. 3, includes a conical distal point 202, a distal sealing ring 204 and a proximal sealing ring 206. The syringe rubber stopper 200 is slidable within the syringe body 104 and in combination with the syringe body 104 defines a pressure chamber. The syringe rubber stopper 200 also includes a proximal end 208 which is connected to the distal end 108 of the threaded plunger 106. The threaded plunger 106 is preferably formed of acetal and includes a thread section of approximately ½-20 UNF.

The threads 107, as illustrated in FIG. 6 of the threaded plunger 106, may be engaged by the half nut 124 which is located within the extension 162 of the left half 152 of the housing 102. When the half nut 124 is engaged with the threaded plunger 106, the threaded plunger 106 may be rotated to drive the syringe rubber stopper 200 within the syringe 104. When the half nut 124 is disengaged from the threads 107, the plunger 106 may be pushed or pulled longitudinally by employing the handle 112. This action serves to slide the syringe rubber stopper 200, as shown in FIG. 3, within the syringe body 104, allowing a rapid increase or decrease in the pressure within the pressure chamber. The half nut 124 is moved into or out of engagement with the threaded plunger 106 by the longitudinal shifting of the actuator blade 122. When the actuator blade 122 is shifted rearward, the half nut 124 engages the threaded plunger 106. When the actuator blade 122 is shifted forward or distally, the half nut 124 disengages from the threaded plunger 106.

Figure 4:
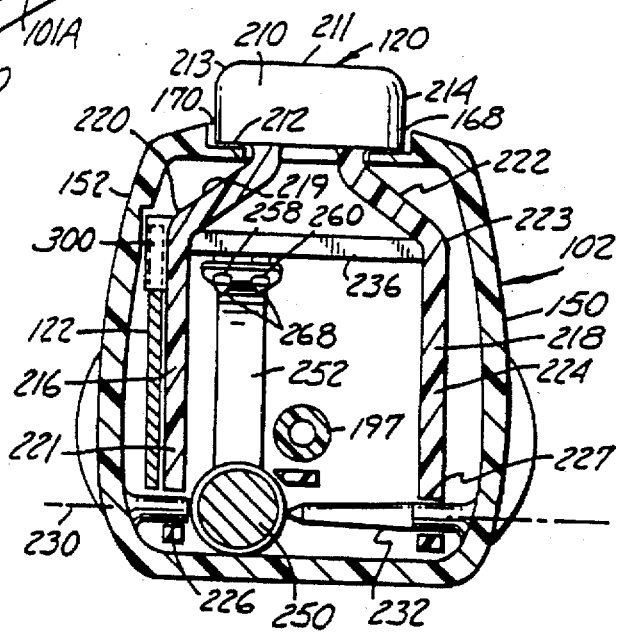
FIG. 4 is a sectional view along line 4—4 of FIG. 2.

The thumb button 120, as shown in FIG. 4, includes an outer body 210 having an upper surface 211, a lower surface 212: a left side 213 and a right side 214. The outer body 210 nests within the inset portions 168 and 170 of the right half 150 and the left half 152. Extending downward from the lower surface 212 is a left arm 216 and a right arm 218. The left arm includes an outward angled portion 219, an elbow 220 and a downwardly directed portion 221. Similarly, the right arm 218 includes an outwardly angled portion 222, an elbow 223 and a downwardly directed portion 224. Distally located on the downwardly extending portion 221 of the left arm 216 is a bore 226. A similar bore 227 is located on the downwardly extending portion 224 of right arm 218. A pivot pin 230 is located inwardly from the left half 152 of the housing 102. A second integral pivot pin 232 of right half 150 of the housing 102 is on the same axis as the first pivot pin 230. The pivot pins 230 and 232 carry the bores 226 and 227 of the left arm 216 and right arm 218. The pivot pins 230 and 232 serve a second function. The gap between the two pivot pins 242 and 244 provides a space for housing a battery 250. A flange 236 connects the left arm 216 and the right arm 218 at elbows 220 and 223. The flange 236 also extends generally distally from the arms 216 and 218. A pair of pins or teeth 268 project downwardly from the flange 236. An oval projection 300 extends outwardly from the elbow 220 of the left arm 216.

As the thumb button 120 pivots on the pivot pins 230 and 232 of the housing 102, the outer body 210 slides within the track created by the insets 168 and 170, as shown in FIG. 5A. The insets 168 and 170 include a distally located rib 237A and a proximally located rib 238A. When the thumb button 120 is pivoted fully forward, the transverse rib 237A engages mating indent 237B on the underside 212 of the outer body 210. In similar fashion, the rearward longitudinal rib 238A is engaged by an indent 238B on the rearmost underside 212 of the outer body 210. In this manner, the thumb button 120 may be reversibly locked in a fully forward or a fully rearward position. In a preferred embodiment, the thumb button is formed of acetal. Preferably, the entire upper surface 211 of the outer body 210 is textured to facilitate movement between the forward position and the rearward position.

Figure 5B:
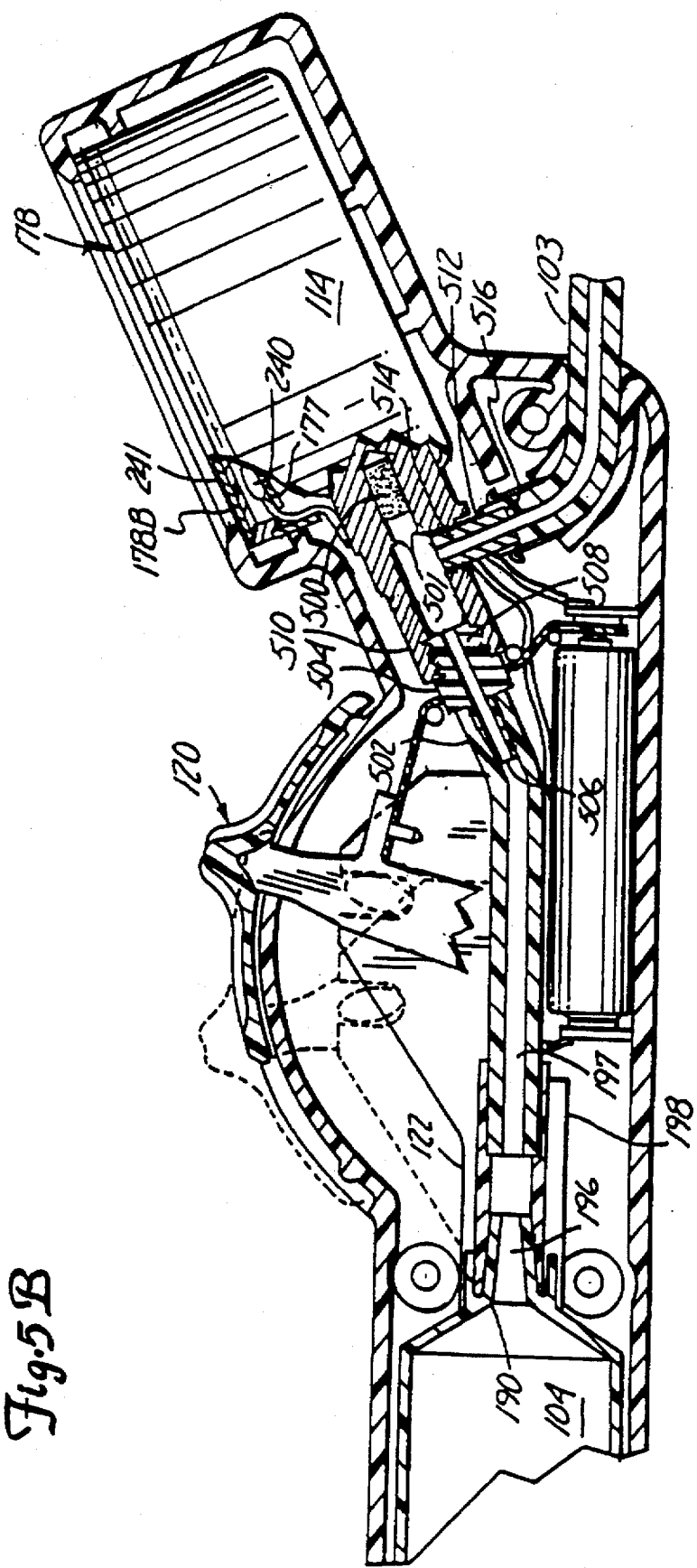

The pressure gauge 114, as illustrated in FIG. 5A, includes a dial face 177 and an incandescent lamp 240. The dial face 177 is spaced apart from and lies under the lens 178. The lamp 240 is glued to an upper surface 177A of the dial face 177 using a cyanoacrylic adhesive. Preferably, the location of the lamp 240 is approximately ¼ inch from the gauge housing 172 and 174; and generally proximal on the dial face 177. Preferably, the lamp 240 is a 1.5 volt lamp which draws approximately 0.0625 amps at 1.25 volts. Suitable lamps are available from Microlamps Co. of Batavia, Ill. A reflector 241 overlies the lamp 240 within the gauge 114. Specifically, the reflector 241 is located on an outside surface 178B of the benzel or lens 178, directly over the lamp 240. The benzel or lens 178 is supplied detached from the gauge 114 or may be removed for ease in gluing the lamp 240 and placing the wires or leads. The reflector 241 serves to both redirect the light produced by the lamp 240 toward the gauge and simultaneously shield the viewer's eyes. The incandescent lamp 240 is connected to a first lead 242 and a second lead 244. The leads 242 and 244 pass between the dial face 177 and the body of the guage 114. In placing the leads 242 and 244, the dial face 177 may be slightly deformed to make a gap. The leads 242 and 244 then exit the gauge near the stem 510 of FIG. 5B. The leads 242 and 244 in turn are connected to a pair of resilient battery terminals 246 and 248. Preferably, the terminals 246 and 248 are formed of beryllium copper alloy and electroplated with tin. A battery 250 is fitted within the housing 102 such that the positive terminal of the battery 250 forms an electrical connection with the resilient battery connector 248 and the negitive terminal is capable of forming an electrical connection or contact with the resilient battery terminal 246. Preferably, the battery 250 is an AAAA size HgZn type battery. Suitable batteries of the type are available from Alexander Manufacturing of Mason City, Iowa. Thus, an electrical circuit is potentially present which includes the battery 250, the lamp 240, the leads 242 and 244, and the resilient terminals 246 and 248.

A flexible insulator strip 252 has a first end 254 initially interposed between the resilient terminal 246 and the negative pole of the battery 250. The opposite end 256 of the flexible insulator strip 252 has a pair of connecting boles 258 and 260, as shown in FIG. 3. The insulator strip 252, as initially installed, prevents the completion of the electrical circuit and thereby preserves the battery 250 until actually needed during an operation. The preferred strip is cut from a 5 mil thickness of Mylar material, although other suitable dielectric material may be substituted. The flexible strip cannot be easily reinserted between the battery 250 and the resilient battery terminal 246 to reinterrupt the circuit. Therefore, once the electrical circuit is completed by removal of the flexible strip 252, the lamp 240 is effectively irreversibly powered until the battery 250 is exhausted.

As initially assembled, the flexible strip 252 has its insertion end 254 between the negative terminal of battery 250 and the resilient battery terminal 246. During assembly, the strip 252 is slid over a first horizontal pin 262 under a second horizontal pin 264 and over a third horizontal pin 266. The connecting holes 258 and 260 of opposite end 256 are attached to the pair of pins or teeth 268 on the flange 236 of the thumb button 120. When the thumb button is pivoted from the forward position, as illustrated in FIG. 5A, toward the rearward position shown by the dotted outline in FIG. 5A, the insulator strip 252 is pulled through the pathway provided by the horizontal pins 262, 264 and 266 such that the inserted end 254 is extracted from between the negative terminal of the battery 250 and the resilient terminal 246. Once removed, reinsertion of the insulator strip 252 is virtually impossible without dismantling the device 100 because of the complex pathway provided by the horizontal pins 262, 264 and 266 and the flexible nature of the insulating strip 252.

The thumb button 120 includes a horizontal projection 300 extending laterally from the thumb button 120. The horizontal projection 300 has a generally oval cross section and includes a first bearing surface 302 generally distally directed and a second bearing surface 304 generally proximally directed. The horizontal extension 300 lies within an upward directed hook 306 distally located on the actuator blade 122. Preferably, the actuator blade is formed of 316 stainless steel. The hook 306 includes a first bearing edge 308 defining a distal extent of the hook 306 and a second bearing edge 310 defining a proximal extent of the hook 306. As the horizontal extension 300 is pivoted proximally, the second bearing surface 304 of the horizontal projection 300 bears against the second bearing edge 310 of the hook 306 thereby shifting the actuator blade 122 in a proximal direction, also shown in FIG. 3 in dotted outline. Similarly, pivoting of the thumb button 120 from the proximal position toward the distal position causes the first bearing surface 302 of the horizontal projection 300 to interact with the first bearing edge 308 of the hook 306 thereby shifting the actuator blade 122 from a proximal position towards a distal position. Because the horizontal projection 300 lies between the outer body 210 and the bores 226 and 227 of the thumb button 120, mechanical advantage is provided to shift the actuator blade 122.

The details of the interaction of the actuator blade 122 and the half nut 124 are illustrated in FIG. 6. The actuator blade 122 includes an offset portion 330 and a transition portion 332. The offset portion 332 serves to hold the half nut 124 in a disengaged position from the threaded plunger 106. When the actuator blade 122 is shifted rearward, as shown in dotted outline, the transition surface 332 forces the half nut 124 into engagement with the threads of the threaded plunger 106.

Figure 7:
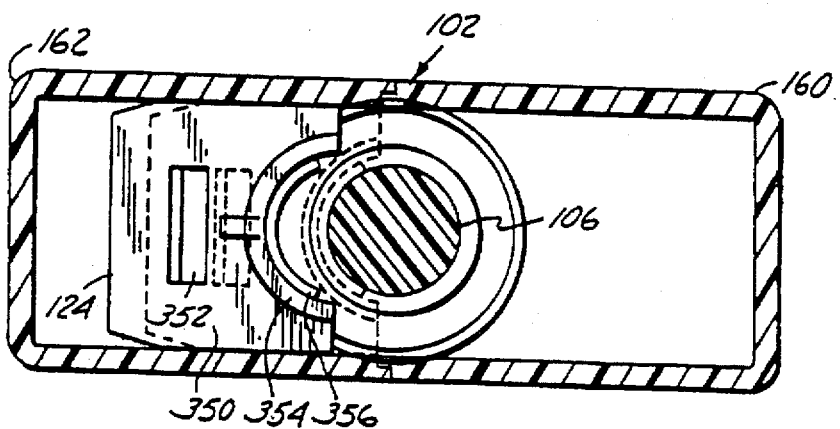
FIG. 7 is a sectional view at line 6—6 of FIG. 2.

In FIG. 7, the half nut 124 is shown in a disengaged position in greater detail. The half nut 124 includes a half nut flange 350 with an actuator blade receiving aperture 352. The actuator blade receiving aperture 352 is sized such that the offset portion 330 of the actuator blade 122 will pass through the receiving aperture 352. The half nut flange 350 slides in a horizontal track 358, as shown in FIG. 6, within the rear extension 162 of the housing 102. A cylindrical portion 354 projects perpendicularly from the flange 350, such that its concave surface faces the threaded plunger 106. The flange 350 and cylindrical portion 354 are further stiffened by a brace 355. Inclined thread surfaces 356 are disposed within the concave surface of the cylindrical portion 354. In FIG. 6, the half nut 124 is also shown engaged by dotted lines. When the half nut 124 is in its engaged position, the threaded portions 356 of the half nut 124 engages the threads of the threaded plunger 106.

The device provides a number of advantages during the performance of an angioplasty procedure. One advantage of the device 100 is the combination of the 20 milliliters syringe body 104 with the relatively fine thread 107 (20 threads per inch) of the threaded plunger 106. A single rotation of the threaded plunger 106 slides the rubber stopper 200 approximately 0.05 inches. In the 20 milliliter syringe body 104, this relatively short advance provides an increase in pressure of approximately 150 psi. Although alternative thread pitches may be employed in the device 100, the choice of relatively "fine" threads 107 in comparison to coarse threads provides more effective fine adjustment of pressure with relatively low effort. Relatively "fine" threads 107 also provide an additional safety feature in that fine threads are less likely to snag or rip a surgical glove than a coarse thread. A rip, snag or tear in a surgical glove is disadvantageous since such an event would be a flaw in the generally sterile atmosphere of the operating room.

Further, a 20 milliliter syringe body 104 is more effective in rapidly deflating a balloon catheter than the smaller (for example 10 milliliter) syringe used in the prior art. Typically, 10 milliliter syringes of the prior art are operated with approximately 2 to 3 milliliters of fluid in the syringe. In contrast, a 20 milliliter syringe body 104 is operated with preferably approximately 5 milliliters of fluid in a syringe. Therefore, a 20 milliliter syringe body 104 allows approximately 15 milliliters to be evacuated, whereas a smaller 10 milliliter syringe allows only approximately 7 milliliters to be evacuated.

An additional advantage of the device 100 is the ability to prime a balloon catheter (when used with the three-way valve 103B). In a typical procedure of the prior art, a 20-milliliter syringe is first employed to prime the catheter by replacing any air with contrast fluid, for example by expanding and contracting the balloon to allow bubbles to work back to the syringe. Subsequently, a smaller 5 or 10-milliliter syringe full of contrast fluid is substituted for the 20-milliliter priming syringe. In contract, the 20-milliliter syringe 104 of the device 100 may be employed to prime a balloon catheter. The air bubbles and excess contrast fluid may then be exhausted at the three-way valve 103B. Thus, the device 100 substitutes for the two differently sized syringes of the prior art procedure.

The unique combination of features present in the device 100 is further emphasized by the explanation of the ease of rapidly deflating a balloon catheter using the device. With the half nut 124 engaged and under controlled high pressure (for example up to as much as 300 psi), the thumb of the hand grasping the housing 102 can pivot the thumb button 120 forward. This has the immediate effect of releasing the pressure on the catheter. The opposite hand may be previously in position on the handle 112 and may immediately pull in the proximal direction, thus evacuating up to approximately 15 milliliters within the syringe body 104. Further, the thumb button 120 may be reengaged in the vacuum position, thereby eliminating the potential fatigue of the physician during the procedure.

A typical gauge 114, when exposed to this rapid pressure fluctuation, could potentially be damaged. The result of such damage might be the potential for inaccurate subsequent readings during the remainder of the procedure. In the device 100, however, typically when primed, a small amount of air remains trapped in the gauge 114 while the remainder of the system is full of renographen or other suitable liquid. In order to protect the gauge 114 from damage from rapid pressure fluctuation, a foam filter 500 which acts as a flow restrictor or shock absorber is placed in the system. The details of the fluid connection are shown in FIG. 5B. The tube 197 leading from the syringe 104 has an opposite end 502 connected to a first tube connector 504. The first tube connector 504 has a 1/16 inch tube fitting 506 inserted within the end 502 of tube 197. The first tube connector 504 also has 10–32 threaded portion 508. The threaded portion 508 is threaded within the brass stem 510 of the gauge 114. A second tube connector 512 has #3–56 threads and is threaded into the stem 510, perpendicular to the first tube connector 504. The second tube 512 is adapted on end 516, opposite the threaded end 514, to connect the catheter connecting tube 103 to the device 100.

Preferably, the foam filter 500 is "stapled" within the stem 510, at a position distal to the second tube connector 512. This may be accomplished by inserting the filter 500, then striking the inside edge of the brass stem 510 with a punch, thereby locking the filter 500 in position by staples 501. Thus, a fluid connection is formed between the syringe 104, the tube 197, the first tube connector 504, the brass steam 510, the second tube connector 512 and the catheter connecting tube 103.

The device 100 also is ergonomically designed. For example, the device 100 is equally functional for right or left-handed use. Additionally, the forward location of the thumb lock 120 reduces the tendency to overshoot a desired pressure. The arrangement of most prior art devices inadvertently encourages overshooting the desired pressure. In the prior art devices, the hand which applies force to the plunger must also serve to engage various locks or valves. Thus, the tendency of a physician is to overshoot a desired pressure and try to quickly move the opposite hand to actuate the valve or catch, thereby saving some of the pressure that had been previously applied. In contrast, the device 100 eliminates that problem by allowing the thumb of the hand gripping the housing 102 to operate the thumb lock 120.

Additionally, as the physician holds the device 100, he can easily view both the gauge 114 and the syringe body 104 contents through the viewing window 167. Further, the relationship between the handle 112 and extensions 160 and 162 of the housing 102, as shown in FIG. 1, is such that a physician's fingers may not be pinched or crushed between the handle 112 and the extensions 160 and 162 of the housing 112.

The T-shaped handle 112 has a relatively comfortable curve which easily fits into the palm of the hand operating the handle 112. Further, in contrast to a round, knob-like handle, the ends of the T-shaped handle provide excellent control of rotational position. The advantage over a round, knob-like handle is that blood inadvertently coating the gloves or the unit cannot render the device inoperable by making the surfaces slippery. The T-handle 112 employed in the device 100 eliminates total reliance upon surface friction to turn the threaded plunger 106. Further, the curved shape of the T-handle 112 provides an efficient grip when pulling in a rearward/proximal direction on the handle 112.

Another feature of the device 100 is the lighted pressure gauge 114. A typical angioplasty procedure lasts approximately two hours or less. The lamp 240 and battery 250 combination of the device is designed to stay lit for approximately four to six hours. Since the preferred embodiment is a disposable unit, a four to six hour lighting duration is more than sufficient for a typical operation. An alternative method of lighting the dial involves the substitution of a chemiluminescent light stick. Such light sticks are also irreversibly activated.

The irreversible activation of the light source is also an advantage of the device 100 since it eliminates the need for an additional switch upon the device 100, further complicating the device.

Additionally, a switch upon the device which could accidentally turn the lighting off during the operation might result in a potential accident if the lighting was extinguished at an inopportune moment. The thumb button 120 (which has the dual purpose of providing an irreversible activation of the lamp 240 and engaging and disengaging the half nut 124) provides a significant mechanical advantage which in turn provides an extremely positive engagement or disengagement of the threads 107. The locking ribs 237A and 238A, together with the indents 237B and 238B of the thumb button 120, enable the positive engagement or disengagement of the half nut 124 to be maintained without a constant application of force. Positive engagement eliminates the possibility of the threaded plunger 106 accidentally slipping rearward and releasing the pressure at an unexpected time during the procedure.

In summary, the device incorporates numerous ergonomic features which save time during a critical operation and additionally tend to prevent fatigue of the physician performing that complex operation. The device as a whole tends to reduce the risk to the patient undergoing the angioplasty procedure.

Figure 9A:
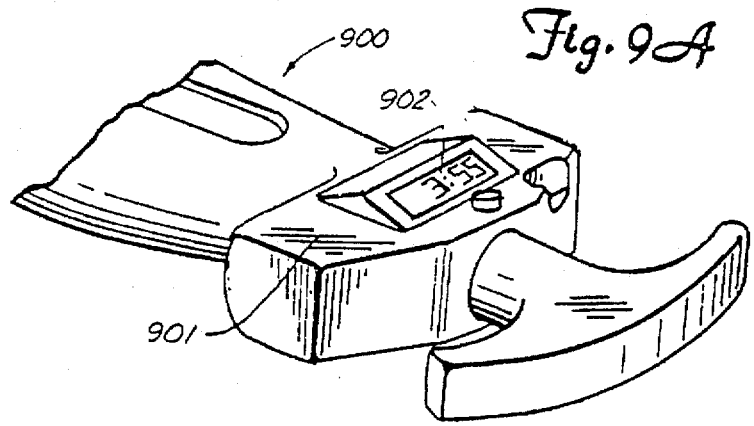
FIGS. 9A, 9B and 9C are perspective, sectional and perspective views of other embodiments of the present invention.
Figure 9B:
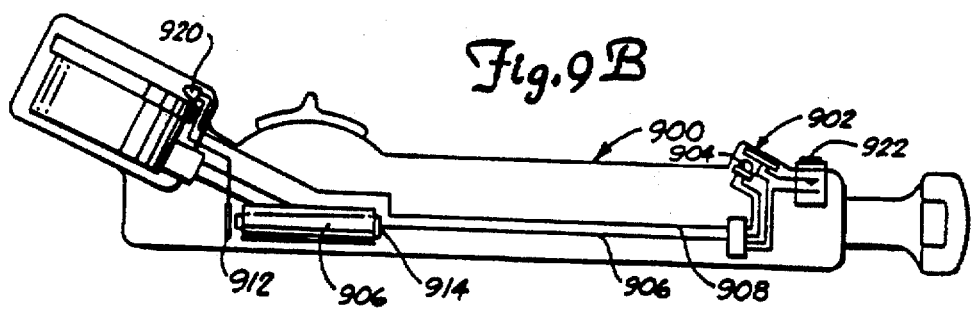
Figure 9C:
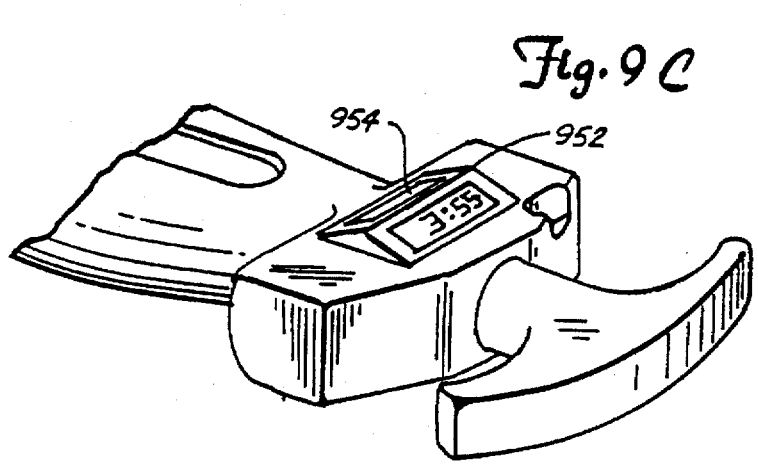

In another embodiment 900 of FIGS. 9A and 9B, the device 900 includes a digital timer 902 located proximally upon the housing 901. The digital timer 902 is a liquid crystal display which is side lit or back lit by a second lamp 904 located under the display. The second lamp 904 and digital timer 902 are powered by the battery 906. The insulated leads 908 and 910 are connected to the resilient battery terminals 912 and 914. The leads 916 and 918 which power the pressure gauge lamp 920 are also connected to the resilient terminals 912 and 914. When the insulating strip (not shown) is extracted from between the resilient terminal 912 and the battery 906, both lamps 904 and 920 and the digital timer 902 are powered. The digital timer 902 further includes a reset button 922. The reset button 922 is located adjacent the timer 902 in a proximal position. Alternatively, a button 954 of FIG. 9C is distally located on the timer 952 in a flush mounted arrangement.

In the angioplasty procedure, the inflated catheter blocks the artery. If the artery is blocked for an excessive period of time, profound ischemia results, which can be extremely painful to the patient. Thus, timing the duration of inflation is critical. The operating physician, however, typically does not wear a watch. Rather, the physician typically relies upon a wall clock. The use of the wall clock is detrimental, however, because the physician must look away from the operation and remember the starting time of each inflation. The digital timer 902 and reset button 922 or 954 eliminates both of these problems.

Figure 10:
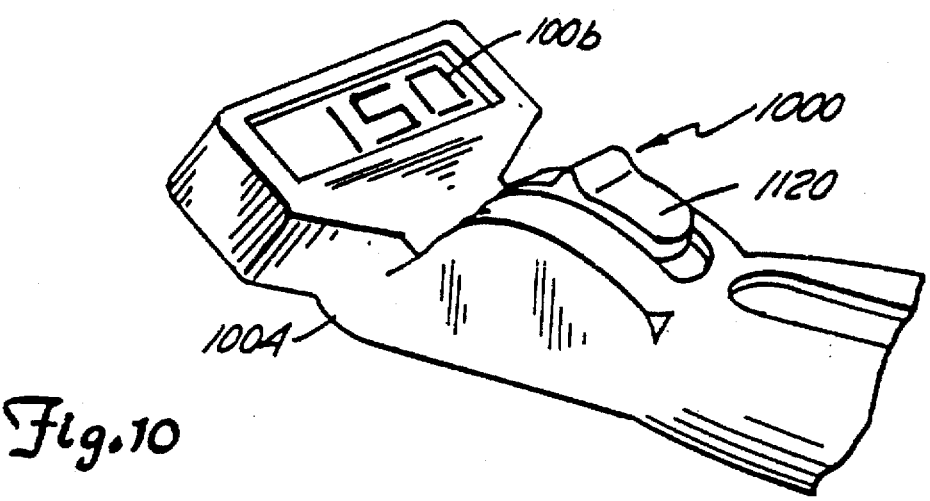
FIG. 10 is a perspective view of a portion of another embodiment of the present invention.

In still another embodiment 1000 of FIG. 10, the device 1000 includes a distal end 1004. A digital pressure display 1006 is included as an alternative to the previously explained dial-type gauge. The digital pressure display 1006 is located adjacent the distal end 1004. The digital pressure display 1006 is powered (as previously shown for the gauge lamp of FIGS. 5A and 5B) by a battery and irreversibly activated by removal of an insulator strip from between the battery and a resilient terminal. A signal, indicative of the pressure, may be supplied by known methods, such as a piezoelectric sensor. The digital pressure display 1006 may also be used in conjunction with a proximally placed electronic sensor as shown in FIG. 9. In this embodiment, a single activation movement of the thumb button 1120 powers both the timer and pressure display 1006.

Although the present invention has been described with reference to preferred embodiments, workers skilled in the art will recognize that changes may be made in form and detail without departing from the spirit and scope of the invention.

What is claimed is:

1. An angioplasty system comprising:

a balloon dilitation catheter and an inflation device, the inflation device comprising:

a barrel having an inside volume of about 20 cc for both priming the balloon catheter and rapidly deflating the balloon catheter;

a plunger disposed inside the barrel, wherein the plunger includes threads disposed thereon;

a housing connected to the barrel;

a means connected to the barrel for providing fluid communication between the barrel and the balloon catheter;

an electric pressure transducer connected to the housing;

an electric display connected to the housing and electrically connected to the pressure transducer;

a battery connected to the housing and electrically connected to the pressure transducer; and an electric timer connected to the housing, the timer including a reset switch for resetting the timer to zero.

2. An angioplasty system as in claim 1, further comprising:

a light connected to the housing.

3. An angioplasty system as in claim 2 wherein the display is angled toward a proximal end of the inflation device.

* * * * *

UNITED STATES PATENT AND TRADEMARK OFFICE
CERTIFICATE OF CORRECTION

PATENT NO. : 5,685,848

DATED : November 11, 1997

INVENTOR(S) : ROBINSON et al.

It is certified that error appears in the above-identified patent and that said Letters Patent is hereby corrected as shown below:

Title page,
item [75] Inventors, "Daniel O. Adams, Blaine" should be --Daniel O. Adams, Orono--; and "William H. Penny, St. Anthony" should be --William H. Penny, Arden Hills--.

At column 5, line 47, ":" should be --,--.

At column 6, line 62, "boles" should be --holes--.

Signed and Sealed this

Ninth Day of March, 1999

Attest:

Q. TODD DICKINSON

*Attesting Officer*        *Acting Commissioner of Patents and Trademarks*